United States Patent
Perovitch et al.

(10) Patent No.: US 9,119,775 B2
(45) Date of Patent: Sep. 1, 2015

(54) USE OF PILOCARPINE FOR HYPOPTYALISM TREATMENT

(76) Inventors: Philippe Perovitch, Le Temple (FR); Marc Maury, Saint Medard en Jalles (FR); Jean Deymes, Bordeaux (FR)

(*) Notice: Subject to any disclaimer, the term of this patent is extended or adjusted under 35 U.S.C. 154(b) by 664 days.

(21) Appl. No.: 13/208,556

(22) Filed: Aug. 12, 2011

(65) Prior Publication Data

US 2011/0301213 A1 Dec. 8, 2011

Related U.S. Application Data

(63) Continuation of application No. 10/585,335, filed as application No. PCT/FR2005/050012 on Jan. 7, 2005, now abandoned.

(30) Foreign Application Priority Data

Jan. 9, 2004 (FR) ................................ 04 50050

(51) Int. Cl.
*A01N 65/00* (2009.01)
*A61K 9/00* (2006.01)
*A61K 36/00* (2006.01)
*A61K 31/4178* (2006.01)

(52) U.S. Cl.
CPC .............. *A61K 9/006* (2013.01); *A61K 31/4178* (2013.01); *A61K 36/00* (2013.01)

(58) Field of Classification Search
CPC ..................................................... A61K 36/00
USPC ......................................................... 424/725
See application file for complete search history.

(56) References Cited

U.S. PATENT DOCUMENTS

| 5,342,840 A | 8/1994 | Hatsuya |
| 5,741,805 A | 4/1998 | Acharya |
| 2001/0043915 A1 | 11/2001 | Frey |
| 2003/0185884 A1* | 10/2003 | Singh et al. .................. 424/465 |

FOREIGN PATENT DOCUMENTS

| FR | 2 737 661 | 2/1997 |
| GB | 941664 | 11/1963 |
| JP | 07330602 | 12/1995 |
| WO | 03/084515 | 10/2003 |

OTHER PUBLICATIONS

Database WPI, Section Ch, Week Apr. 1994, Derwent Publications Ltd., London, GB; AN 1994-034733, XP002292717 & WO 94/1108 A1 (Theratech Inc) Jan. 20, 1994 abstract.
Rosas J et al: "Usefulness of basal and pilocarpine-stimulated salivary flow in primary Sjogren's syndrome. Correlation with clinical, immunological and histological features," Rheumatology (Oxford), vol. 41, No. 6, Jun. 2002, pp. 670-675, XP002292716, ISSN: 1462-0324 p. 674.
Resolution Oneo, May 2001, 5 pages.

* cited by examiner

*Primary Examiner* — Michael Meller
(74) *Attorney, Agent, or Firm* — Young & Thompson

(57) ABSTRACT

A method of treating hypoptyalism in a subject is provided. The method includes administering to the subject a pharmaceutical composition that includes pilocarpine and a bioadhesive polymer. The composition dissolves sublingually in the mouth of the subject and adheres to mucous tissues in the buccopharyngeal cavity. The pilocarpine then dissolves and binds to muscarine receptors present in cells of the subject's salivary glands, endobuccal submucous glands and submaxillary glands, is then absorbed by the cells thereby stimulating the glands to produce saliva.

9 Claims, No Drawings

USE OF PILOCARPINE FOR HYPOPTYALISM TREATMENT

CROSS REFERENCE TO RELATED APPLICATIONS

This application is a continuation of application Ser. No. 10/585,335 filed on May 20, 2008; which is the 35 U.S.C. 371 national stage of International application PCT/FR05/50012 filed on Jan. 7, 2005; which claimed priority to French application 0450050 filed Jan. 9, 2004. The entire contents of each of the above-identified applications are hereby incorporated by reference.

BACKGROUND OF THE INVENTION

This invention relates to a composition for the treatment of hypoptyalism comprising pilocarpine. This composition has direct multiple effects in the buccopharyngeal cavity.

The problems produced by xerostomia are numerous and are well-known without satisfactory solutions having been provided. Radiotherapy is one of the main treatments in the case of cancers of the ORL cavity that leads to significant undesirable effects.

The consequences of this dryness of the mouth are in particular problems in the acts of swallowing and speaking that may result in anorexia.

It is suitable to analyze, however, prior to the study of solutions provided by the composition according to this invention, the various mechanisms that are brought into question. Salivary production is dependent upon:
- primary salivary glands: parotid, submaxillary and sublingual, and
- secondary salivary glands that are disseminated over the entire surface of the oral mucous membrane: labial, jugal, palatine and velar, lingual and sublingual.

These two stages are themselves distributed in three histological structures:
- serous glands,
- mucous glands, and
- mixed or seromucous glands.

The origins of the hypoptyalism can be broken down into:
- Transitory hypoptyalism: pre-menopausal or menopausal state, medicinal doses such as oral contraceptives, diuretics, cardiovascular products, anti-inflammatory products, antihistamines, antidepressants, psychotropes, tranquilizers, antiparkinsonian agents, and
- Permanent hypoptyalism: development of autoimmune ailments, Gougerot-Sjögren syndrome that affects the exocrine and mucous glands, iatrogenic effects produced by treatment with therapeutic irradiation generating a deficit that can still be compensated by a therapeutic stimulation.

Within the framework of treatments and stimulations of these mechanisms, the pilocarpine that is an alkaloid extract from the leaves of *pilocarpus* of the different varieties *jaborandi, pennatifolius*, and *microphyllus* is known.

It appears that the pilocarpine of composition $C_{11}H_{16}N_2O_2$ is a liquid that is oily, viscous, and sensitive to light and that exhibits an amphiphilic nature that allows dissolution both in water and much more easily in a solvent or a composition of organic solvents.

This parasympathomimetic active ingredient stimulates the secretions of the exocrine glands and therefore the secretions of the salivary glands and the sweat glands.

The *Jaborandi* dye is obsolete and never received marketing approval because it is impossible to determine with precision the content of active ingredient. Moreover, as for any dye, other elements or components or substances that are exogenic and that are not the object of any study will be found to be present. The stability of the product and the preservation methods can also be discussed.

In current pharmacopoeia, pilocarpine is known as an active ingredient in oral form and medicines are currently marketed.

In the administration of these medicines, it should be noted that the dose is 5 mg of pilocarpine per tablet to be administered 3× per day, or 15 mg of pilocarpine per day, and even up to 30 mg per day for certain more severe cases. Actually, it has been noted that this taking of large doses conducted over several weeks is at the origin of significant undesirable secondary effects such as nausea, excessive sweating, sensations of dizziness, hot flashes or asthenias.

A primary consequence of the oral method is the passage through the digestive tract that leads to variable absorption and bioavailability because the first hepatic passage subjects the active ingredient to a significant degradation in the form of metabolites that no longer have pharmacological activities. It is therefore necessary to provide an overdosage so that the effect of the existing portion reaches the oral and submaxillary activity zones.

Another consequence is a delayed effect of the active ingredient since the first action of the pilocarpine is exerted only with a delay of 0.45 to 1 hour after intake.

The composition that includes the pilocarpine according to this invention makes it possible to greatly limit the secondary effects that are linked to an absorption by an oral path, improves the dose/effect ratio and imparts a strong improvement of the bioavailability.

The invention is now described in detail according to a particular, non-limiting embodiment with an illustration by examples of suitable galenical forms.

The composition according to this invention consists in administering pilocarpine in basic form or in the form of salts, chlorohydrate or nitrate, in a specific galenical form of a tablet with sublingual usage with slow disintegration allowing it:
- to directly and instantaneously access the muscarine-like receptors of the submucous glandular structures,
- to protect itself and to be stable with regard to the light, the temperature and the oxidation,
- to dissolve and to be attached locally by thoroughly combining with tissues of the buccopharyngeal cavity.

To this end, the pilocarpine is combined with at least one bioadhesive polymer, at least one buffer, and at least one lubricant.

A softener and a hydrophilic substance can be combined with these agents, and the formulation in tablet form can provide dimensions that can prevent the act of swallowing and the direct passage to the digestive tract.

A formulation example of a tablet for sublingual use is:

| | |
|---|---|
| pilocarpine that is basic or in salt form: | 2.5 mg |
| magnesium stearate: | 10.0 mg |
| sodium or disodium hydrogen phosphate: | 90.0 mg |
| K 100 methocel: | 50.0 mg |
| 6 000 polyethylene glycol: | 40.0 mg |
| hyaluronic acid: | 20.0 mg |
| lysozyme chlorohydrate: | 15.0 mg |
| compressed sorbitol qsp for 1000 mg: | 772.5 mg |

The pH buffer with a sodium or disodium hydrogen phosphate base can be replaced by sodium carbonate or sodium bicarbonate.

Magnesium stearate is a lubricant that is suitable for the production of tablets, and PEG, in addition to its lubricating properties, is hydrophilic, imparting a softening effect to the composition.

It is also possible to cite the family of cellulose derivatives, gums or other polymers as substances that have the same functionalities as PEG.

The family of cellulose derivatives comprises in particular:
sodium carboxy-methyl cellulose,
hydroxy-ethyl cellulose,
hydroxy-propyl cellulose,
hydroxy-propyl methyl cellulose,
hydroxy-propyl methyl promellose,
methyl cellulose or metolose, or
carboxy-methyl cellulose.

Among the gums, it is possible to cite:
guar,
xanthane, or
arabic gum.

Polymers that are suitable for this application comprise:
alginic acid and derivatives,
carboxy-vinyl polymer
carbomer
macrogols
gelatin
povidone, or
pectins.

The lysozyme chlorohydrate can advantageously be added so as to compensate for the deficit of physiological salivary lysozyme in the case of the hypoptyalism. The dosage can be adapted but a range of proportions is between 5 and 30 mg for a 1000 mg tablet.

Another element for better use of the pilocarpine in the local application according to this invention is the use of a mass substrate that has low molecular weight and is preferably hygroscopic.

It is possible to cite the family of polyols, sorbitol, mannitol or xylitol, but also glucose or lactose. This hygroscopic nature induces the execution of liquid movements from the oral cavity to this mass substrate facilitating the dissolution of the pilocarpine, the distribution and the adhesion to mucous tissues.

The composition according to this invention leads to positive consequences that are now listed.

Thanks to the composition according to this invention, the pilocarpine creates a first direct effect because it is immobilized upon direct contact of the muscarine-like receptors that are present within various salivary gland structures, endobuccal submucous glands and submaxillary glands.

The pilocarpine, thus kept in contact, is well-enough dissolved and bioavailable to be absorbed through the phospholipid structures of the walls of the cells of the stratified epithelium of the mucous membrane.

Due to the local presence of the pilocarpine, an increase of the local micro-vascular flow with a sensation of heat and therefore an increase of the local tissue absorption are also noted. The effect is self-fed and makes it possible to start up the salivary production immediately.

This first effect that is obtained is direct but not only does the pilocarpine access the saliva production groups, but it also passes partly into the sublingual and perlingual venous microvascularization.

This portion of the pilocarpine, thus absorbed by the mucous membrane, rejoins the systemic circulatory flood.

Consequently, for the general circulation, the pilocarpine is found distributed in several minutes to submaxillary glandular bundles, which constitutes a second action that is slightly offset over time and arises from a different mechanism.

This formulation thus makes it possible to avoid the passage through the liver and the associated metabolization. The amount can be reduced and the dose/effect ratio is greatly increased.

Moreover, the passage through the stomach whose pH also alters the pilocarpine is avoided.

The pilocarpine that causes these two successive effects is therefore extremely advantageous.

In addition, the effects of stimulation according to the known pharmacokinetic studies extend over a duration of several hours on the order of 4 to 8 hours.

Actually, several milligrams of pilocarpine, from 2 to 25 mg per day, for clarification, are adequate in using this formulation.

The dose reduction induces a potential economy of secondary effects. The effective concentration thresholds of the composition according to this invention are much lower and often less than the triggering thresholds on the digestive, cardiovascular or urinary level and the thresholds for creating excessive sweating, hot flashes or nausea.

As to the pilocarpine remaining circulating in the arterial path, necessarily in a very small amount, it always rejoins the hepatic system via the hepatic artery and is ultimately metabolized. This makes it possible to comply with the detoxification metabolism.

The treatment with small doses and a perfectly stable formulation also makes it possible to use a very adjustable dosage, more specifically adapted to each patient based on requirements that are often very variable, with values adjusted to nearly 0.5 mg.

Such a formulation thus allows an intake of pilocarpine in a permanent manner because the side effects are reduced.

In terms of the action, it is understood that the stimulation treatment of the two stages of the salivary production of the patient suffering from hypoptyalism is very effective and makes the patient more comfortable.

Thus, this double effect that is offset over time in the immediate production by the oral sub-mucous membrane upon contact followed by the stimulation of the large glands, parotid glands and submaxillary glands of the salivary system allows eating under good conditions of salivary response.

The invention claimed is:

1. A method of treating hypotyalism in a human in need thereof, comprising:
administering sublingually to said human in need thereof a therapeutically effective amount of a pharmaceutical composition comprising magnesium stearate, pilocarpine and a bioadhesive polymer combined in the form of a tablet,
wherein the pilocarpine is the form of a salt, chlorohydrate or nitrate, and
the bioadhesive polymer is:
a cellulose derivative selected from the group consisting of sodium carboxy-methyl cellulose, hydroxy-ethyl cellulose, hydroxy-propyl cellulose, hydroxy-propyl methyl cellulose, hydroxy-propyl methyl promellose, methyl cellulose, and carboxy-methyl cellulose,
a gum selected from the group consisting of guar, xanthan, and arabic gum,
a polymer selected from the group consisting of alginic acid, carboxy-vinyl polymer, carbomer, macrogol, gelatin, povidone, and pectin,
or combinations thereof, wherein the tablet dissolves when placed sublingually in the mouth of the human;

allowing the tablet to dissolve sublingually in the mouth of the human, wherein the composition locally adheres to and thoroughly combines with mucous tissues in a buccopharyngeal cavity of the human;

allowing the pilocarpine to dissolve and bind to muscarine receptors present in cells of the human's salivary glands, endobuccal submucous glands and submaxillary glands, the bound pilocarpine then being absorbed by the cells of the human through the receptors and stimulating said glands to produce saliva, without said pilocarpine having to pass through the stomach or the liver of the human.

2. The method according to claim 1, wherein the composition comprises:

2.5 mg pilocarpine in salt form,
10.0 mg magnesium stearate,
90.0 mg sodium or disodium hydrogen phosphate,
50.0 mg methyl cellulose,
40.0 mg polyethylene glycol 6000,
20.0 mg hyaluronic acid,
15.0 mg lysozyme, and
772.5 mg compressed sorbitol.

3. The method according to claim 2, wherein the sodium or disodium hydrogen phosphate is replaced by sodium carbonate or sodium bicarbonate in the same proportions.

4. The method according to claim 1, wherein the composition comprises 0.20-2.5% by weight pilocarpine in salt form.

5. The method according to claim 1, wherein the composition comprises 0.20-0.25% by weight pilocarpine in salt form.

6. The method according to claim 1, wherein the composition comprises 0.05-0.30% by weight lysozyme.

7. The method according to claim 1, wherein the composition further comprises a buffer, a lubricant, a softening agent, a hydrophilic substance and a hygroscopic substrate.

8. The method according to claim 1, wherein the composition comprises pilocarpine in salt form, methylcellulose, sodium or disodium hydrogen phosphate, magnesium stearate, hyaluronic acid, polyethylene glycol, and sorbitol.

9. The method according to claim 1, wherein the bioadhesive polymer is a cellulose derivative selected from the group consisting of sodium carboxy-methyl cellulose, hydroxy-ethyl cellulose, hydroxy-propyl cellulose, hydroxy-propyl methyl cellulose, hydroxy-propyl methyl promellose, methyl cellulose, carboxy-methyl cellulose, and combinations thereof, the composition further comprising sodium (bi)carbonate, compressed sorbitol, and a buffer.

* * * * *